United States Patent
Hayes et al.

(10) Patent No.: US 10,512,422 B2
(45) Date of Patent: Dec. 24, 2019

(54) LOCATION DETECTION SYSTEMS AND METHODS

(71) Applicant: Stryker Corporation, Kalamazoo, MI (US)

(72) Inventors: Michael Joseph Hayes, Kalamazoo, MI (US); Krishna Sandeep Bhimavarapu, Kalamazoo, MI (US); Jonathan Mark Greenbank, Plainwell, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 15/988,373

(22) Filed: May 24, 2018

(65) Prior Publication Data

US 2018/0263533 A1 Sep. 20, 2018

Related U.S. Application Data

(62) Division of application No. 15/075,747, filed on Mar. 21, 2016, now Pat. No. 9,999,375.

(60) Provisional application No. 62/145,276, filed on Apr. 9, 2015.

(51) Int. Cl.
*A61B 5/11* (2006.01)
*A61B 5/00* (2006.01)
*G16H 40/67* (2018.01)

(52) U.S. Cl.
CPC .......... *A61B 5/1115* (2013.01); *A61B 5/0022* (2013.01); *A61B 5/6891* (2013.01); *A61B 5/6892* (2013.01); *G16H 40/67* (2018.01)

(58) Field of Classification Search
CPC ... A61B 5/1115; A61B 5/0022; A61B 5/6891; A61B 5/6892; G16H 40/67
USPC ...................................................... 340/539.13
See application file for complete search history.

(56) References Cited

U.S. PATENT DOCUMENTS

| | | | |
|---|---|---|---|
| 2006/0279427 A1* | 12/2006 | Becker ................. | A61B 5/0002 340/573.4 |
| 2007/0141869 A1* | 6/2007 | McNeely ............. | A61B 5/0006 439/76.1 |
| 2007/0210917 A1* | 9/2007 | Collins, Jr. ........... | A61B 5/1117 340/539.1 |
| 2008/0172789 A1* | 7/2008 | Elliot ..................... | G06F 19/00 5/616 |

(Continued)

Primary Examiner — Omar Casillashernandez
(74) Attorney, Agent, or Firm — Warner Norcross + Judd LLP

(57) ABSTRACT

A location detection system identifies the locations of medical devices such as patient support apparatuses and/or patient care devices within a medical facility. The devices communicate via a wired connection to one or more medical facility systems (e.g. nurse call system, computer network, etc.), and/or via a wireless connection to such systems. The location detection system automatically determines location information of the devices and communicates the location information so that the recipient of any outgoing alerts and/or other information sent from the devices is apprised of the location of the particular device sending the alert or other information. Caregivers are thereby able to respond to the correct location of an alert, and software systems such as EMR systems, admission discharge and transfer (ADT) systems, etc. are able to correlate transmitted device data with the location and/or patient assigned to that location.

10 Claims, 8 Drawing Sheets

(56) References Cited

U.S. PATENT DOCUMENTS

| | | | |
|---|---|---|---|
| 2009/0063183 A1* | 3/2009 | McNeely | A61G 12/00 705/2 |
| 2012/0092135 A1* | 4/2012 | Collins, Jr. | A61B 5/1115 340/10.1 |
| 2013/0135160 A1* | 5/2013 | Dixon | H01Q 1/44 343/720 |
| 2014/0039351 A1* | 2/2014 | Mix | A61B 5/1114 600/587 |

\* cited by examiner

LOCATION DETECTION SYSTEMS AND METHODS

CROSS-REFERENCE TO RELATED APPLICATIONS

This application is a divisional of U.S. patent application Ser. No. 15/075,747 filed Mar. 21, 2016, by inventors Michael Joseph Hayes et al. and entitled LOCATION DETECTION SYSTEMS AND METHODS, and this application claims priority to U.S. provisional patent application Ser. No. 62/145,276 filed Apr. 9, 2015 by inventors Michael Hayes et al. and entitled LOCATION DETECTION SYSTEMS AND METHODS, the complete disclosures of both of which are hereby incorporated herein by reference.

BACKGROUND

The present disclosure relates to patient support apparatuses (e.g. beds, stretchers, cots, recliners, etc.), and patient care devices, and more particularly to systems and methods for determining and communicating the location of the patient support apparatuses and/or patient care devices within medical facilities.

Patient support apparatuses and patient care devices used in medical facilities often are designed to include one or more alerts states and/or to generate data that is desirably communicated to another location within the healthcare facility (e.g. a nurses' station, an electronic medical records (EMR) server, to mobile devices carried by individuals, etc.). In order for the alerts and/or data to be meaningful to the recipient, it is typically desirable to identify the room number or other location identifier that indicates where the patient support apparatus or patient care device is currently positioned.

SUMMARY

The present disclosure relates to improved manners of identifying the location of medical devices such as patient support apparatuses and/or patient care devices within a medical facility. The various aspects of the disclosure are applicable to devices that communicate via a wired connection to a medical facility system (e.g. nurse call system, computer network, etc.), as well as devices that communicate via a wireless connection to one or more medical facility systems, and in some cases, devices that communicate via both wired and wireless connections. Aspects of the disclosure allow the locations of such devices to be determined automatically and communicated off the device so that the recipient of the outgoing alerts and/or other information from the device is apprised of the location of that particular device. This allows caregivers to respond to the correct location of an alert, as well as software systems (e.g. EMR systems, admission discharge and transfer (ADT) systems, etc.) to correlate the received data with the location and/or patient assigned to that location.

According to one aspect, a location detection system is provided that includes a mobile patient support apparatus and a stationary module positioned at a known location with a healthcare facility. The mobile patient support apparatus has a first unique identifier, a sensor, and a first wireless transceiver. The mobile patient support apparatus is adapted to transmit via the first wireless transceiver the unique identifier and at least one signal that is based on data from the sensor. The stationary module includes a second unique identifier and a second wireless transceiver that is adapted to receive both the first unique identifier and the signal from the mobile patient support apparatus. The stationary module also includes a third wireless transceiver that is adapted to transmit the first and second unique identifiers to a wireless access point of a computer network. The stationary module further includes a wired transceiver that is adapted to transmit the signal over a cable to a nurse call system.

In other embodiments, the stationary module does not transmit the first unique identifier over the cable to the nurse call system, but instead exclusively transmits the first unique identifier over the third wireless transceiver.

The first and second wireless transceivers operate in accordance with the Institute of Electrical and Electronics Engineers (IEEE) standard 802.15.1 (e.g. Bluetooth), and the third wireless transceiver operates in accordance with IEEE standard 802.11 (e.g. WiFi), in some embodiments.

The stationary module further includes, in some embodiments, a fourth wireless transceiver, and the mobile patient support apparatus further includes a fifth wireless transceiver that is adapted to communicate with the fourth wireless transceiver. In some of such embodiments, the fourth and fifth wireless transceivers are infrared transceivers.

In still other embodiments, the mobile patient support apparatus also includes a sixth wireless transceiver adapted to communicate with the wireless access point of the computer network. In such embodiments, the stationary module is adapted to transmit the second unique identifier to the mobile patient support apparatus using the fourth wireless transceiver, and the mobile patient support apparatus is adapted to not communicate the second unique identifier using the sixth wireless transceiver.

The signal that is transmitted over a cable to a nurse call system indicates that a patient positioned on the mobile patient support apparatus may be exiting the mobile patient support apparatus, in at least one embodiment.

According to other aspects, the wired transceiver is in communication with a first port of the stationary module that is adapted to physically couple to a first end of the cable, and a second end of the cable is adapted to physically couple to a second port of the nurse call system.

In some embodiments, the stationary module is contained within a housing adapted to be mounted to a wall of a hospital room.

In at least one embodiment, the mobile patient support apparatus is a bed, the sensor is a switch adapted to detect activation of a nurse call button on the bed, and the signal indicates that a patient on the bed desires to speak with a nurse. The bed may further include a microphone and be adapted to transmit audio signals from the microphone to the stationary module using the first wireless transceiver. In such cases, the stationary module is adapted to transmit the audio signals to the nurse call system via the wired transceiver.

The bed may further include a scale adapted to detect a patient's weight, wherein the bed is adapted to transmit the patient's weight using the first wireless transceiver. In such cases, the stationary module is adapted to transmit the patient's weight to a server on the computer network using the third wireless transceiver.

In some embodiments, the mobile patient support apparatus further includes a fourth wireless transceiver adapted to communicate with the wireless access point of the computer network. The mobile patient support apparatus transmits status data regarding the mobile patient support apparatus to the computer network using the fourth wireless transceiver.

The location detection system is configured in some embodiments to include a second mobile patient support apparatus. The stationary module is adapted to receive a third unique identifier from the second mobile patient support apparatus and to transmit the second and third unique identifiers to the wireless access point. The stationary module receives the third unique identifier via the third wireless transceiver.

According to another embodiment, a location detection system is provided that includes a stationary module and a mobile patient support apparatus. The stationary module is positioned at a fixed and known location within a facility. The stationary module includes a first unique identifier and a first wireless transceiver adapted to transmit the first unique identifier. The mobile patient support apparatus has a second unique identifier and a second wireless transceiver. The mobile patient support apparatus is adapted to receive the first unique identifier from the stationary module via the second wireless transceiver.

In some embodiments, the mobile patient support apparatus further includes a data table that correlates the first unique identifier to the known location within a healthcare facility. The mobile patient support apparatus transmits the known location to a wireless access point of a computer network using a third wireless transceiver. The data table correlates the first unique identifier to a room number of the healthcare facility. Still further, in some embodiments, the mobile patient support apparatus is adapted to receive the data table from a server coupled to the computer network. The data table is received at the mobile patient support apparatus via the third wireless transceiver. In some embodiments, the mobile patient support apparatus requests the data table from the server in response to a triggering event.

In other aspects, the mobile patient support apparatus only transmits the known location to the wireless access point of the computer network if the mobile patient support apparatus and the stationary module successfully link to each other utilizing fourth and fifth wireless transceivers. The fourth and fifth wireless transceivers have a shorter communication range than the first and second wireless transceivers.

According to another embodiment, a location detection system is provided that includes a mobile patient support apparatus and a stationary module. The mobile patient support apparatus has a first unique identifier and a first wireless transceiver. The mobile patient support apparatus is adapted to transmit the first unique identifier via the first wireless transceiver. The stationary module is positioned at a fixed location within a healthcare facility and includes a second unique identifier and a second wireless transceiver adapted to receive the first unique identifier from the mobile patient support apparatus. The stationary module also includes a data table that correlates the first unique identifier to the fixed location within the healthcare facility.

In some embodiments, the stationary module is adapted to transmit the fixed location and the first unique identifier to a wireless access point of a computer network using a third wireless transceiver. The stationary module is also adapted to transmit the fixed location to the mobile patient support apparatus via the second wireless transceiver, in some embodiments.

According to other aspects, the stationary module receives the data table from a server coupled to the computer network. The stationary module receives the data table via the third wireless transceiver.

In some embodiments, the transmission of the fixed location to the wireless access point includes transmitting a room number of a room that includes the fixed location.

According to another embodiment, a patient support apparatus system is provided that includes a stationary module, an off-board device, and a patient support apparatus having a support surface for supporting a patient thereon, a first transceiver for communicating with the stationary module, a second transceiver for communicating with the off-board device, and a controller. The controller is adapted to transmit a unique identifier corresponding to the patient support apparatus to both the stationary module and the off-board device. The controller uses the first transceiver to communicate the unique identifier to the stationary module, and the controller uses the second transceiver to communicate the unique identifier to the off-board device.

In some embodiments, the off-board device is a server located on a healthcare facility computer network, the first transceiver is a Bluetooth transceiver, and the second transceiver is a WiFi transceiver. Further, in some embodiments, the stationary module forwards the unique identifier to the server using a third transceiver positioned on-board the stationary module.

The stationary module transmits a unique stationary module identifier to the server, in some embodiments, and the server uses the unique stationary module identifier and the unique identifier to determine the location of the patient support apparatus within the healthcare facility.

According to still another embodiments of the disclosure, a patient support apparatus system is provided that includes an off-board device and a patient support apparatus having a support surface for supporting a patient thereon, a first transceiver for communicating with the off-board device, a second transceiver for communicating with the off-board device, and a controller. The controller is adapted to transmit a first data item to the off-board device using the first transceiver, and to transmit a second data item to the off-board device using the second transceiver. The first data item is different from the second data item.

In some embodiments, the off-board device is a server located on a healthcare facility computer network.

The first data item is a unique identifier corresponding to the patient support apparatus and the second data item is a status of a component of the patient support apparatus, in at least some embodiments. The status of the component may be any one or more of the following: a position of a siderail, a state of a brake, a height of the support surface, and a state of an exit detection system.

In some embodiments, the patient support apparatus is further adapted to transmit the first data item to the off-board device using the second transceiver.

According to still another embodiment of the disclosure, a patient support apparatus system is provided that includes a stationary module and a patient support apparatus. The stationary module includes a first transceiver, a second transceiver, and a third transceiver. The patient support apparatus includes a support surface for supporting a patient thereon, a fourth transceiver for communicating with the first transceiver of the stationary module, and a controller. The controller is adapted to transmit a data item to the stationary module using the fourth transceiver, and the stationary module is adapted to forward the data item to both a first destination using the second transceiver and to a second destination using the third transceiver.

In some embodiments, the first destination is a headwall connector of a nurse call system, and the second destination is a server located on a healthcare facility computer network. The second transceiver may be a wired transceiver and the third transceiver may be a wireless transceiver.

The data item indicates that an alert has issued regarding the patient support apparatus, in some embodiments.

The patient support apparatus may be further adapted to transmit a second data item to the stationary module using the fourth transceiver, and the stationary module may be further adapted to forward the second data item to only one of the first and second destinations. The second data item is a unique identifier corresponding to the patient support apparatus, in at least some embodiments.

Before the various embodiments disclosed herein are explained in detail, it is to be understood that the claims are not to be limited to the details of operation or to the details of construction and the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

DETAILED DESCRIPTION OF THE EMBODIMENTS

Figure 1:
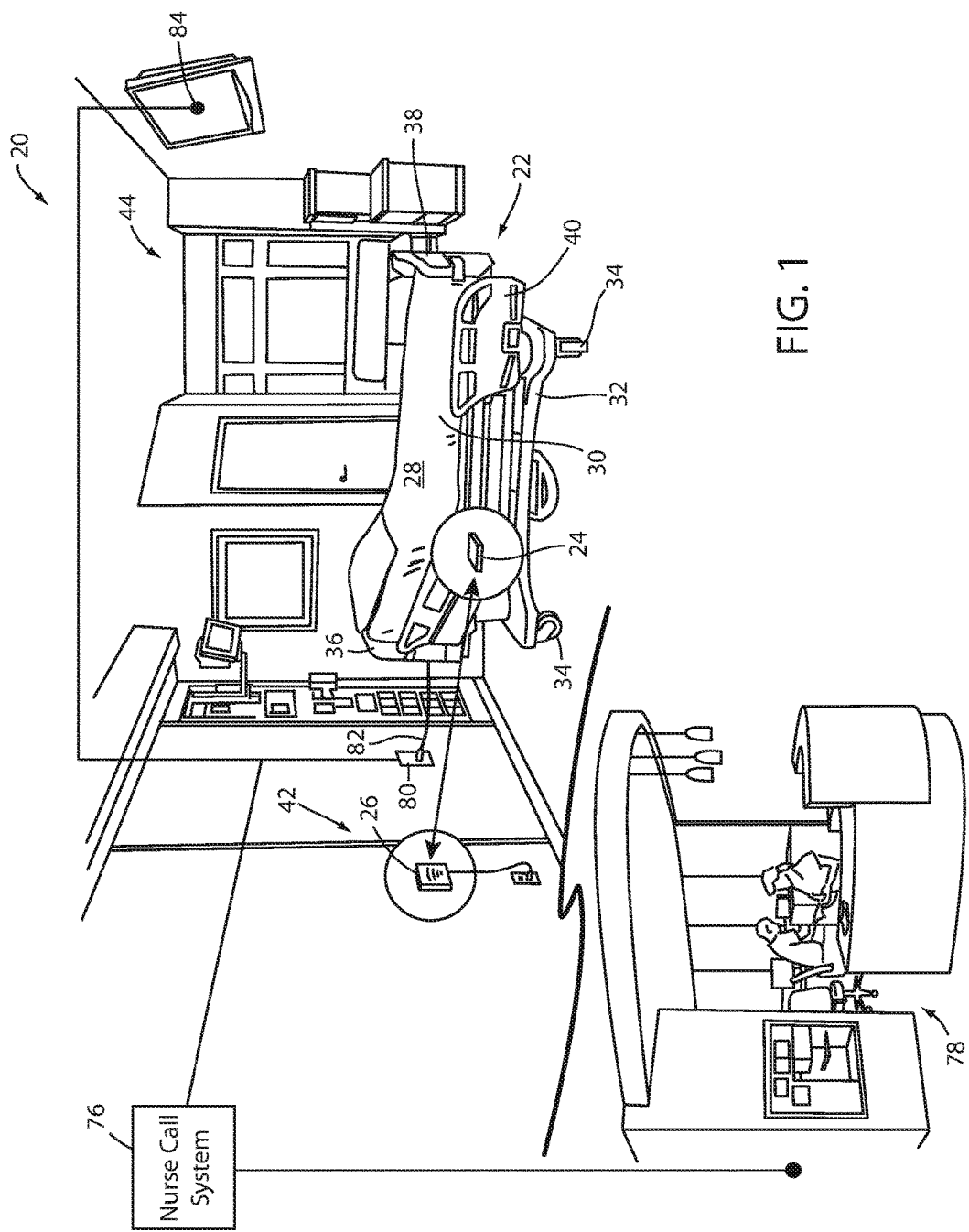
FIG. 1 is a perspective view of a location detection system for a mobile patient support apparatus according to a first embodiment of the disclosure.

An illustrative example of a location detection system 20 according to a first embodiment is shown in perspective view in FIG. 1. Location detection system 20 includes a mobile patient support apparatus 22 having a mobile wireless unit 24 and a stationary module 26. For purposes of visual description herein, patient support apparatus 22 is shown in the accompanying drawings as a hospital bed, but it will be understood that patient support apparatus 22 can be alternatively implemented as a cot, stretcher, chair, recliner, or other apparatus that is capable of supporting a person. Indeed, location detection system 20 can be applied to determine the location of other types of medical devices besides patient support apparatuses, such as, but not limited to, thermal management systems such as shown in commonly assigned U.S. patent application Ser. No. 14/282,383 filed May 20, 2014 by inventors Christopher J. Hopper et al. and entitled THERMAL CONTROL SYSTEM, the complete disclosure of which is hereby incorporated herein by reference.

Patient support apparatus 22 of FIG. 1 includes a support surface 28 on which a mattress 30 is positioned to allow a person to lie or sit thereon. Patient support apparatus 22 further includes a base 32 having a plurality of wheels 34 that allow patient support apparatus 22 to be moved to different locations. Still further, patient support apparatus 22 of FIG. 1 includes a headboard 36, a footboard 38, and a plurality of siderails 40.

The construction of patient support apparatus 22 may take on a wide variety of different forms. In some embodiments, other than the components described below, patient support apparatus 22 is constructed in any of the manners described in commonly assigned, U.S. Pat. No. 8,689,376 issued Apr. 8, 2014 by inventors David Becker et al. and entitled PATIENT HANDLING DEVICE INCLUDING LOCAL STATUS INDICATION, ONE-TOUCH FOWLER ANGEL ADJUSTMENT, AND POWER-ON ALARM CONFIGURATION, the complete disclosure of which is hereby incorporated herein by reference. In other embodiments, those components of patient support apparatus 22 not described below are constructed in any of the manners described in commonly assigned, U.S. patent application Ser. No. 13/775,285 filed Feb. 25, 2013 by inventors Guy Lemire et al. and entitled HOSPITAL BED, the complete disclosure of which is also hereby incorporated herein by reference. Still further, in other embodiments, those components of patient support apparatus 22 not described below are constructed in any of the manners disclosed in commonly assigned, U.S. patent application Ser. No. 14/212,009 filed Mar. 14, 2014 by inventors Christopher Hough et al., and entitled MEDICAL SUPPORT APPARATUS. In still other embodiments, patient support apparatus 22 takes on other constructions.

Figure 3:
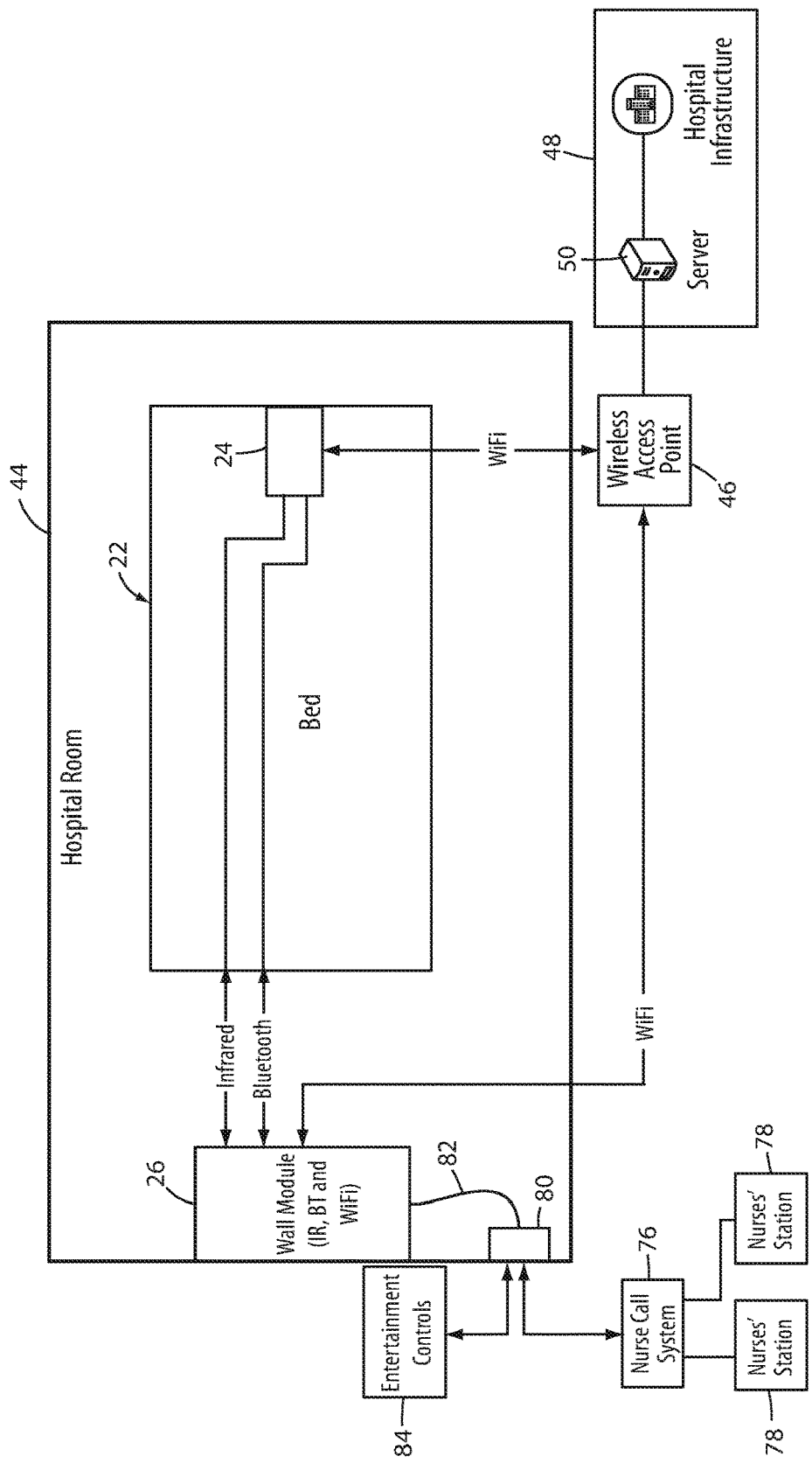
FIG. 3 is a block diagram of the location detection system of FIG. 2 shown with the patient support apparatus implemented as a bed and with the system coupled to an illustrative example of a healthcare facility's information technology (IT) infrastructure.

As shown in FIG. 1, patient support apparatus 22 further includes mobile wireless unit 24. Mobile wireless unit 24 is adapted to wirelessly communicate with stationary module 26. Stationary module 26 is mounted to a fixed and known location within a healthcare facility, such as, but not limited to, a headwall 42 of a room 44. As will be discussed in greater detail below, mobile wireless unit 24 and stationary module 26 are adapted to establish a communication link that allows the location of patient support apparatus 22 within the facility to be determined and/or communicated to one or more off-board devices/systems. In one embodiment, stationary module 26 includes a unique identifier that is transmitted to a wireless access point 46 of the healthcare facility's network 48 (FIG. 3). Stationary module 26 also receives a patient support apparatus identifier that corresponds to a unique patient support apparatus 22 when the patient support apparatus 22 is positioned within close proximity (e.g. within about 5-10 feet) to stationary module 26. Stationary module 26 also forwards this unique identifier to the wireless access point 46. One or more servers 50 on the computer network 48 include a map or data table that correlates the location of each stationary module 26 with each room, bed bay, or other specific location within the healthcare facility. Upon receipt of the unique stationary module identifier 98 and the unique patient support apparatus identifier, the server 50 consults the map or data table and determines that that particular patient support apparatus 22 is in the location of the particular stationary module 26 that transmitted the identifiers. In at least one embodiment, as will be discussed further below with respect to FIG. 3, the patient support apparatus 22 does not send any additional data to the stationary module 26 that is forwarded to server 50 other than the unique identifier or patient support apparatus 22. Any further data from patient support apparatus 22 that is to be forwarded to server 50, or another device on network 48, is forwarded from patient support apparatus 22 directly to wireless access point 46 without passing through stationary module 26.

Figure 2:
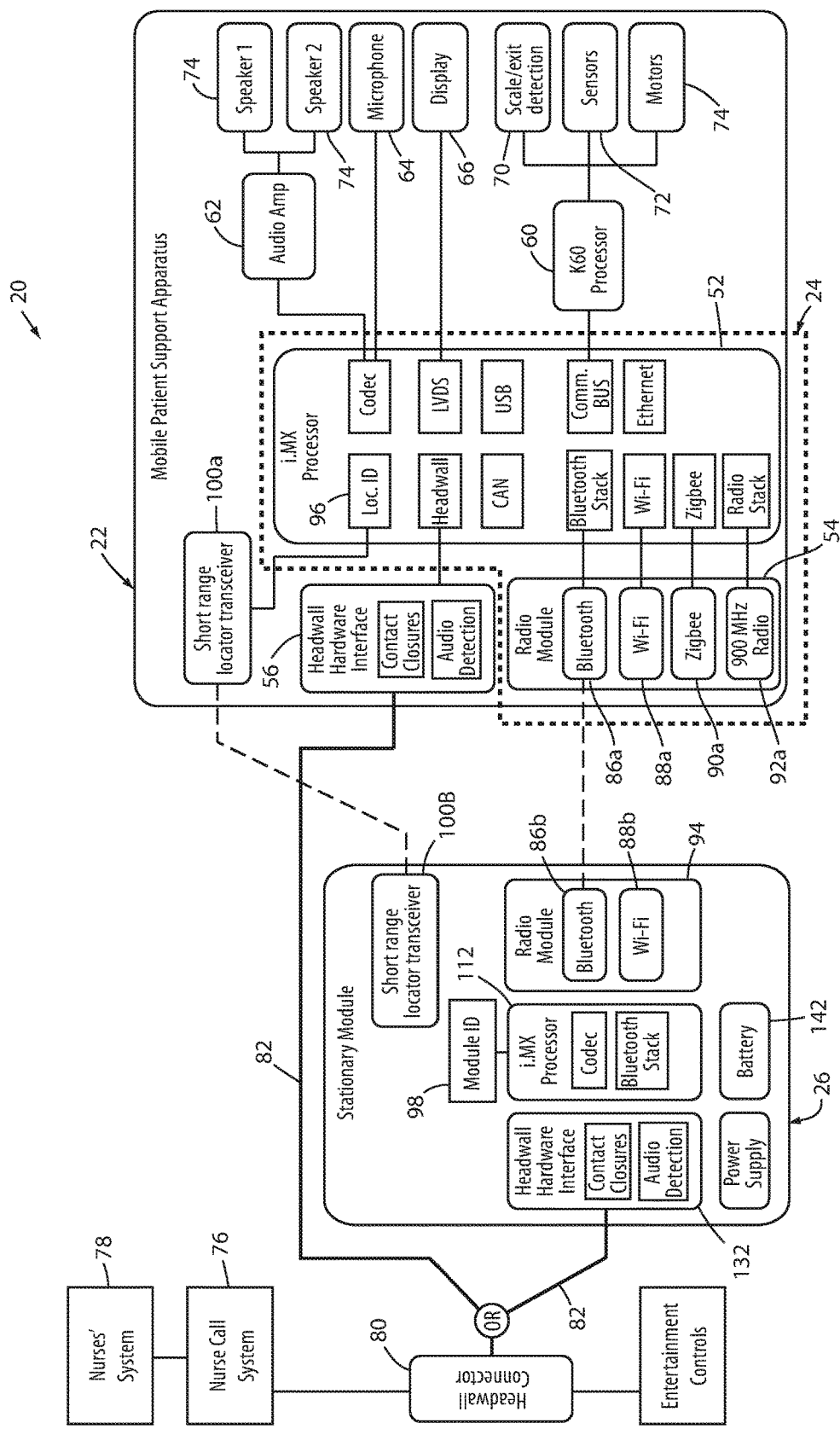
FIG. 2 is a block diagram of the internal components of the various structures of the location detection system of FIG. 1.

One example of the internal components of both mobile wireless unit 24 and stationary module 26 is shown in FIG. 2. As can be seen, mobile wireless unit 24 includes a controller 52 that is in electrical communication with a radio module 54, as well as a headwall hardware interface 56, a mobile locator transceiver 58, a main patient support apparatus controller 60, an audio amplifier 62, a microphone 64, and a display 66. Audio amplifier 62, in turn, is in electrical communication with one or more speakers 68. Controller 52 of mobile wireless unit 24, as well as main controller 60 of patient support apparatus 22, may take on a variety of different forms, such as, but not limited to, commercially available off-the-shelf microcontrollers.

For example, in one embodiment, controller 52 is any one of the i.MX family of system-on-chip (SoC) processors, and main controller 60 is anyone of the Kinetis K60 family of microcontroller units (MCUs), both of which are marketed by Freescale Semiconductor of Austin, Tex. Other types of commercially available microcontrollers may also be used. Still further, controllers 52 and 60 may take on still other forms, such as any combination of any one or more microprocessors, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. The instructions followed by controllers 52 and 60 in carrying out the functions described herein, as well as the data necessary for carrying out these functions, are stored in one or more accessible memories (not shown).

Main controller 60 is responsible for carrying out the overall operations of patient support apparatus 22, while controller 52 is responsible for carrying out the communication between patient support apparatus 22 and stationary module 26. In some embodiments, a single controller that combines the functions of main controller 60 and controller 52 is used. In the embodiment shown in FIG. 2, main controller 60 is in communication with one or more indicators scale/exit detection system 70, one or more sensors 72, and one or more motors 74. Scale/exit detection system 70 is adapted to measure the weight of a patient support on patient support apparatus 22 and/or to detect when the patient is about to exit, or has exited, patient support apparatus 22. In at least one embodiment, scale/exit detection system 70 is a combined scale and exit detection system that is constructed and designed in the manner disclosed in commonly assigned U.S. Pat. No. 5,276,432 issued to Travis and entitled PATIENT EXIT DETECTION MECHANISM FOR HOSPITAL BED, the complete disclosure of which is hereby incorporated herein by reference.

Sensors 72 include sensors that are adapted to detect parameters of patient support apparatus 22, such as, but not limited to, the status of a brake for wheels 34; the height of support surface 28 relative to base 32; the status (raised or lowered) of one or more siderails 40; the armed or disarmed state of exit detection system 70; and/or other parameters. Motors 74 provide movement to one or more components of patient support apparatus 22, such as, but not limited to, raising and lowering the height of support surface 28 relative to base 32, and/or raising and lowering one or more sections of support surface 28. As will be discussed in greater detail below, main controller 60 is adapted to forward information from one or more of sensors 72 to controller 52 of mobile wireless unit 24 for forwarding to either stationary module 26 or to wireless access point 46.

Controller 52 of mobile wireless unit 24, in addition to being in communication with main controller 60, is also in communication with audio amplifier 62 for purposes of delivering audio signals to speakers 68. Such audio signals include the audio signals received by mobile wireless unit 24 from stationary module 26 that correspond to the voice of a caregiver who is speaking from a remote location, such as a nurses' station 78, to an occupant of patient support apparatus 22. Further, in some embodiments, controller 52 may send audio signals to audio amplifier 62 and speakers 68 that are received from other sources, such as from a server (e.g. server 50 or some other server) located on local area network 48 of the healthcare facility in which patient support apparatus 22 is positioned.

When an occupant of patient support apparatus 22 wishes to speak to a caregiver at a remote location via the facility's nurse call system 76, he or she speaks into microphone 64. Controller 52 digitizes the audio signals from microphone 64 and forwards them to either radio module 54 or to headwall interface 56, depending upon what type of wired connection exists at a nearby headwall connector 80. A cable 82 runs from headwall connector 80 to either stationary module 26 or to patient support apparatus 22, depending upon how a particular healthcare facility has decided to implement location detection system 20. If cable 82 runs between patient support apparatus 22 and headwall connector 80, controller 52 forwards the digitized audio signals to headwall hardware interface 56, which in turns forwards them over cable 82 to headwall connector 80. If cable 82 runs between headwall connector 80 and stationary module 26, then controller 52 forwards the digitized audio signals to radio module 54, which in turn wirelessly transmits them to stationary module 26. Stationary module 26 then forwards them to headwall connector 80 via cable 82.

Radio module 54 detects when a wireless link exists between itself and stationary module 26. A message indicating the existence or non-existence of this link is forwarded by radio module 54 to controller 52. Similarly, headwall hardware interface 56 also detects when a wired link (e.g. cable 82) is present between interface 56 and headwall connector 80. Headwall hardware interface 56 forwards a message to controller 52 indicating the existence or non-existence of this link. Controller 52 utilizes these messages from radio module 54 and interface 56 to determine how to route data that is to be transmitted off of patient support apparatus 22.

Headwall connector 80 is part of, or electrically coupled to, a conventional nurse call system 76. Headwall connector 80 is a conventional connector that often includes 37 pins adapted to be inserted into 37 mating sockets of cable 82, or vice versa. Such 37 pin connections are one of the most common types of connectors found on existing headwalls of medical facilities for making connections to the nurse call system 76 and/or environmental controls 84 (e.g. television, temperature, curtains, etc.). Such 37 pin connectors, however, are not the only type of connectors, and it will be understood that headwall connector 80 can include a different number of pins.

Mobile wireless unit 24 communicates wirelessly with stationary module 26 via radio module 54. In the embodiment illustrated in FIG. 2, radio module 54 includes four separate transceivers: a Bluetooth transceiver (IEEE 802.15.1) 86*a*, a WiFi transceiver (IEEE 802.11) 88*a*, a ZigBee transceiver (IEEE 802.15.4) 90*a*, and a 900 MHz transceiver 92*a*. It will be understood that the number of transceivers within radio module 54 can vary from the four shown in FIG. 2, and that the protocols used for the transceivers can take on different forms than those illustrated in FIG. 2. Radio module 54 communicates wirelessly with a radio module 94 contained within stationary module 26. In the illustrated embodiment, radio module 94 includes two transceivers: a Bluetooth transceiver 86*b* that communicates with Bluetooth transceiver 86*a* of mobile wireless unit 24 and a WiFi transceiver 88*b* that communicates with wireless access point 46 (FIG. 3). In some alternative embodiments, stationary module 26 also includes a ZigBee transceiver 90*b* that communicates with ZigBee transceiver 90*a* of mobile wireless unit 24 and a 900 MHz transceiver 88*b* that communicates with 900 MHz transceiver 88*a* of mobile wireless unit 24.

In addition to the components previously described, mobile patient support apparatus 22 includes a unique identifier 96 (FIG. 2) that distinguishes one patient support apparatus 22 from another, and also, in some embodiments, distinguishes a specific patient support apparatus 22 from other types of patient care devices that may be utilizing location detection system 20. Stationary module 26 also includes a unique identifier 98 that distinguishes each particular stationary module 26 from other stationary modules 26. At the time of installation of location detection system 20, stationary modules 26 are mounted at fixed locations throughout a healthcare facility, such as, but not limited to, headwalls 42 in patient rooms. Once mounted, the locations of each stationary module 26 within the facility are surveyed and stored electronically in a data table or map. As will be discussed more below, this data table or map is stored, in at least some embodiments, on server 50. In other embodiments, however, it is stored elsewhere and/or duplicated and stored in multiple locations.

Mobile patient support apparatus 22 and stationary module 26 each further include a short range locator transceiver 100*a* and 100*b*, respectively. In at least one embodiment, short range locator transceivers 100*a* and 100*b* are infrared transceivers that are able to communicate with each other when they are positioned in line of sight with each other, and within a relatively short range of each other, such as, but not limited to, five to ten feet. Short range locator transceivers 100*a* and 100*b*, identifiers 96 and 98, and the data table or map are used to determine the location of patient support apparatus 22 within a facility in several different manners, one of which is explained in more detail below with reference to FIGS. 3 and 4.

Figure 4:
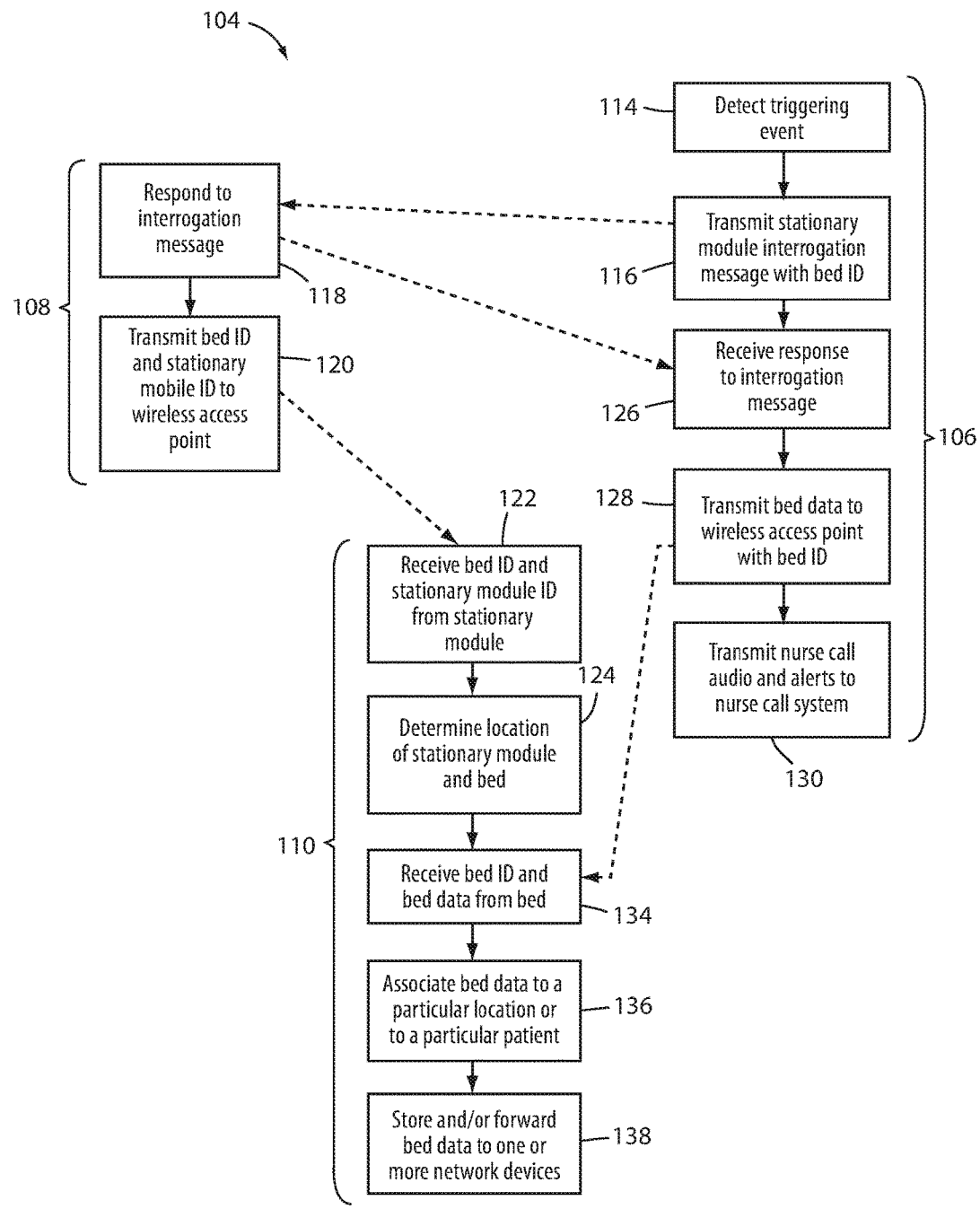
FIG. 4 is a flowchart of the location detection algorithm followed by the components of the location detection system of FIG. 2.

FIG. 3 illustrates an illustrative example of a first embodiment of a location detection system 20 that is configured for determining the location of a patient support apparatus 22 that is implemented as a bed. FIG. 4 illustrates a flowchart of steps taken by various components of the location detection system 20 of FIG. 3 that are used to determine which room 44 (and/or bay) patient support apparatus 22 of FIG. 3 is located in. More specifically, FIG. 4 illustrates a first location detection algorithm 104 executed by location detection system 20 according to a first embodiment. Location detection algorithm 104 includes three components: a patient support apparatus algorithm 106, a stationary module algorithm 108, and a server algorithm 110. Patient support apparatus algorithm 106 is executed by controller 52 of patient support apparatus 22. Stationary module algorithm 108 is executed by a controller 112 (FIG. 2) on board stationary module 26. Server algorithm 110 is executed by a server located outside of room 44, such as, but not limited to, server 50.

Location detection algorithm 104 begins at an initial step 114 when patient support apparatus 22 detects a triggering event. The specific triggering event may vary. In some embodiments, the triggering event is the application of the brakes on board patient support apparatus 22. In other embodiments, the triggering event is the plugging in of an AC power cable on board the patient support apparatus 22 to an AC wall outlet. In still other embodiments, the both of these events are triggering events and/or still other triggering events are used.

Regardless of the specific triggering event, once it is detected by patient support apparatus 22, controller 52 moves onto step 116 where it sends out an interrogation signal. The interrogation signal is sent out via short range locator transceiver 100*a* and is configured to be detected by a stationary module 26. Because it is sent out via short range transceiver 100*a*, it is only detected by a stationary module 26 if the patient support apparatus 22 is within close proximity to stationary module 26 (e.g. within the same room, or adjacent a particular bay within a room if the room is semi-private and adapted to accommodate multiple patients). The interrogation signal includes patient support apparatus ID 96.

Short range locator transceiver 100*b* of stationary module 26 receives the interrogation signal from patient support apparatus 22 and passes it to controller 112. Controller 112 executes stationary module algorithm 108 in response to receipt of this interrogation signal. Controller 112 begins this algorithm at step 118, where it responds to the interrogation signal. This response is sent from stationary module 26 via short range locator transceiver 100*b*. In at least one embodiment, this response includes the patient support apparatus identifier 96 that was received at stationary module 26 from patient support apparatus 22 in the interrogation message. This identifier 96 is used to address the response to the specific patient support apparatus 22 that broadcast the interrogation signal at step 116. This ensures that, in the unlikely event that multiple patient support apparatuses 22, or other medical devices, are within communication range of stationary module 26, the response message is processed by only the originator of the interrogation message.

After responding to the interrogation message at step 118, controller 112 of stationary module 26 proceeds to step 120 where it transmits both the patient support apparatus identifier 96 and its stationary module ID 98 to server 50. This transmission is done wirelessly, in at least one embodiment. More specifically, in at least one embodiment, controller 112 uses WiFi transceiver 88*b* to transmit the identifiers 96 and 98 from stationary module 26 to a wireless access point 46 (FIG. 3) of healthcare facility network 48. Once the identifiers 96 and 98 reach access point 46, they are forwarded via the internal routing procedures of network 48 to server 50, which is part of the network 48.

Server 50 begins server algorithm 110 at step 122 when it receives the identifiers 96 and 98 from stationary module 26 via network 48 and wireless access point 46. Server 50 uses the identifiers 96 and 98 to determine the location of the patient support apparatus 22 within the healthcare facility at step 124. This is done with reference to the data table or map described previously that was generated during installation of stationary modules 26. As noted, this data table identifies the room and/or bays of each stationary module 26 with the healthcare facility. When server 50 receives a particular pair of identifiers 96 and 98, its looks in the table to determine where in the healthcare facility the stationary module 26 having that particular identifier 98 is located. Once the location of that particular stationary module 26 is identified, server 50 associates that location with the patient support apparatus 22 having the identifier 96 that was transmitted with the identifier 98. In other words, upon receipt of a message from a particular stationary module 26 wherein the message includes that particular stationary module identifier 98 and a corresponding patient support apparatus identifier 96, server 50 concludes that the particular patient support apparatus 22 having ID 96 is located at the same location as that particular stationary module 26. This conclusion is justified because, as noted earlier, patient support apparatus 22 is only able to communicate with stationary module 26 when it is within close range, and indeed, is unable to communicate with other stationary modules 26 that may be within the same room, but are positioned at other bays or other designated areas. Thus, the fact that patient support apparatus 22 was able to forward its ID 96 to module 26, which in turn forwarded it to server 50, is an indication that patient support apparatus is located close to module 26.

Returning to the patient support apparatus algorithm 106, controller 52 of patient support apparatus 22 proceeds to step 126 after transmitting its interrogation signal at step 116. At step 126, patient support apparatus 22 awaits receipt of a message from stationary module 26 acknowledging receipt of its interrogation signal. Once patient support apparatus 22 receives this acknowledgement at step 126, controller 52 of patient support apparatus 22 considers patient support apparatus 22 and stationary module 26 to be linked together.

After this linkage is established, controller 52 moves to step 128 where it transmits patient support apparatus data to server 50 via WiFi transceiver 88a (FIGS. 3 and 4) and wireless access point 46. Such data includes status data regarding any one or more of the following components of patient support apparatus 22: siderails 40 (e.g. up or down), a brake for wheels 34 (e.g. braked or unbraked), support surface 28 (e.g. its height), scale/exit detection system 70 (e.g. whether the system is armed, disarmed, alerting, or not alerting), sensors 72, motors 74, and still other components. Such data may also include data regarding the patient, such as the patient's weight, the patient's vital signs, one or more therapies or protocols performed on the patient while on or near the patient support apparatus 22, and other patient data. Regardless of its specific content, the transmission of such data by patient support apparatus 22 at step 128 includes the transmission of patient support identifier 96.

In addition to transmitting patient support status at step 128 to server 50, controller 52 of patient support apparatus 22 also transmits nurse call audio and alerts to nurse call system 76, as appropriate. The transmission of such audio and/or alerts takes place in one of two different manners. When a cable 82 is connected between headwall hardware interface 56 of patient support apparatus 22 and headwall connector 80, controller 52 transmits the patient support apparatus status data at step 130 first to headwall hardware interface 56, which forwards the information via cable 82 to headwall connector 80, and from there it is passed to nurse call system 76. Alternatively, if a cable 82 is connected between stationary module 26 and headwall connector 80, controller 52 transmits the patient support apparatus status data at step 130 first to radio module 54, which forwards the data wirelessly to radio module 94 of stationary module 26. (This latter situation is illustrated in FIG. 3, although it will be understood that the location of cable 82 in FIG. 3 can be modified to extend directly from patient support apparatus 22 to connector 80). From radio module 94, controller 112 of stationary module 26 forwards the data to a headwall hardware interface 132 of stationary module 26. Headwall hardware interface 132 forwards the data via cable 82 to connector 80, which then passes the data to nurse call system 76. In at least one embodiment, the transmission of such data from radio module 54 to radio module 94 takes place via a Bluetooth protocol (e.g. IEEE 802.15.1).

At step 134 of server algorithm 110, server 50 receives the data from patient support apparatus 22. After receiving this data, server 50 proceeds to step 136 where it associates the data it received at step 134 with either the location of stationary module 26 or a particular patient associated with patient support apparatus 22. Such location association is carried out using the pairing of identifiers 96 and 98 that were received by server 50 at step 122. That is, when server 50 receives identifiers 96 and 98 at step 122, it knows that the patient support apparatus 22 with the identifier 96 is located at the location of stationary module 26, and that any future data received from the patient support apparatus 22 with identifier 96 at step 134 is data coming from the location of the stationary module 26 having the identifier 98.

If server 50 associates the data received at step 136 with a particular patient, rather than a location, it does so by consulting another database that maintains a log of the current locations of particular patients within the healthcare facility. This database may be stored in another server on network 48, such as an Admission, Discharge, and Tracking (ADT) server, or some other server, which forwards the relevant information to server 50. In other embodiments, this database may be stored elsewhere. Regardless of its location, server 50 uses this database correlating patients to locations to associate the data received at step 136 with a particular patient.

Once the data received at step 136 is associated with either a location or a patient (or both), server 50 proceeds to step 138 where it stores the received data and/or forwards it to one or more other network devices (e.g. servers). For example, in at least one embodiment, server 50 is configured to automatically forward patient information to an electronic medical records (EMR) server. In such an embodiment, server 50 associates the incoming data from a particular patient support apparatus 22 at step 134 with a patient identifier at step 136. Once associated, server 50 forwards this data to the EMR server for entry into that particular patient's electronic medical record.

In the embodiments shown and described with respect to FIGS. 3 and 4, the stationary module identifier 98 is never forwarded from patient support apparatus 22 to server 50 via the WiFi transceiver 88a on-board patient support apparatus 22. Instead, as noted, stationary module identifier 98 is forwarded to server 50 from stationary module 26 itself.

From the description provided herein of the location detection system 20 of FIGS. 3 and 4, it can be seen that patient support apparatus 22 forwards its identifier 96 to two different entities using two different types of transceivers. That is, it forwards its identifier 96 to short range locator transceiver 100b using its own short range locator transceiver 100a, and it also forwards its identifier 96 to server 50 via WiFi transceiver 88a and wireless access point 46. Although forwarded to two different entities using two different communication protocols, the identifier 96 arrives at the same destination: server 50. Server 50, as noted above, uses the identifier 96 to determine the location of the patient support apparatus 22 using the message received from stationary module 26. Server 50 also uses the identifier to determine what location and/or patient to associate the data with that it receives from patient support apparatus 22 at step 134.

Figure 5:
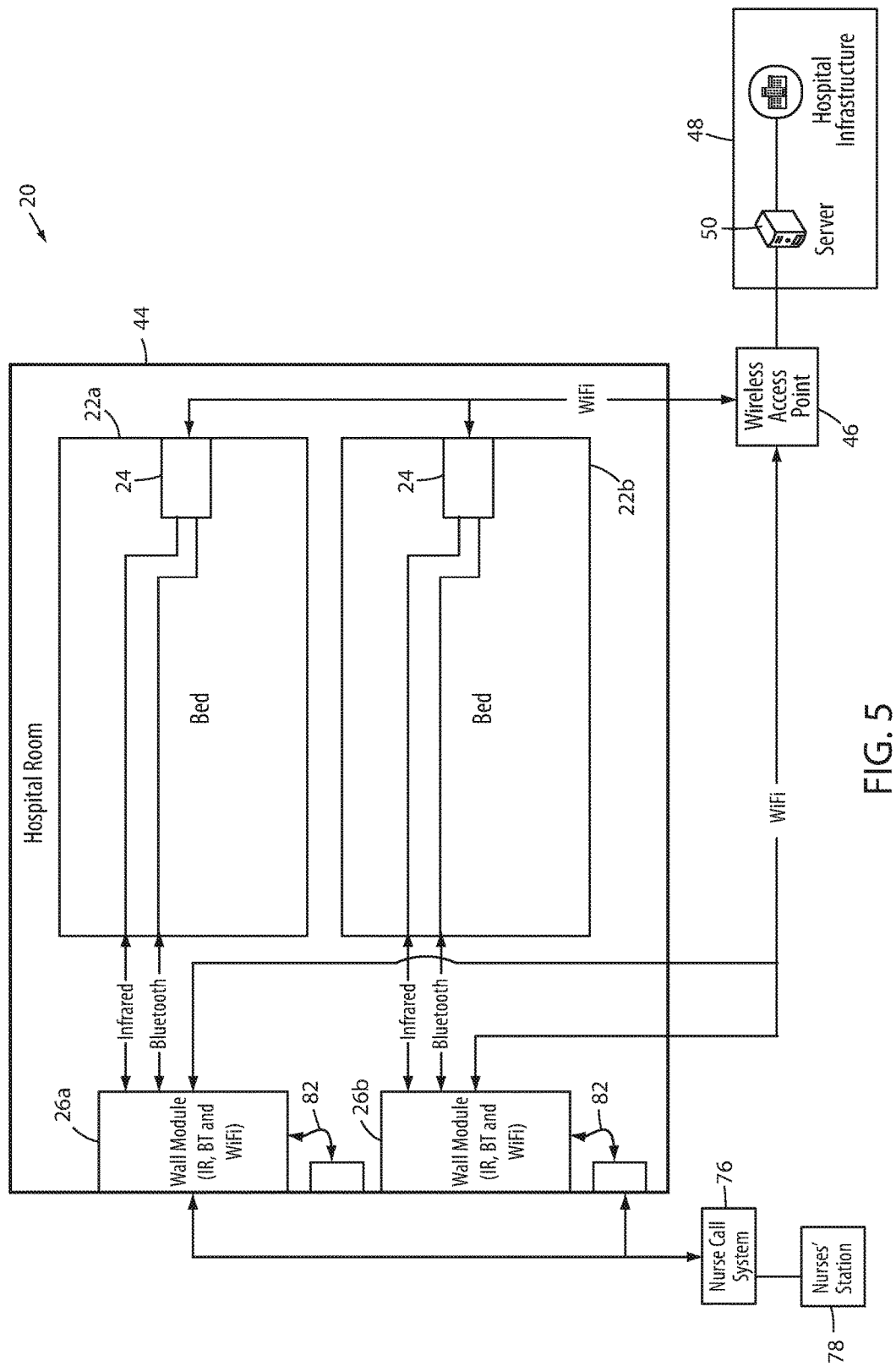
FIG. 5 is a block diagram of the location detection system of FIG. 2 expanded to determine the location of multiple patient support apparatuses.

It will be understood that, in a typical healthcare facility, server 50 will be in communication with a plurality of stationary modules 26 and associated patient support apparatuses 22. One such example is shown in FIG. 5. Room 44 of FIG. 5 includes a first patient support apparatus 22a and a second patient support apparatus 22b. Patient support apparatus 22a and patient support apparatus 22b each individually carry out algorithm 106 (FIG. 4). Similarly, stationary modules 26a and 26b each individually carry out algorithm 108. Server 50, in turn, carries out algorithm 110 with respect to each of these different support apparatuses 22a, 22b, and modules 26a, 26b. That is, server 50 determines the locations of each of support apparatuses 22a and 22b and associates the data received from each of them at step 134 either with their location or with the patient who is associated with support apparatuses 22a and 22b. Location detection system 20 can, of course, be applied to facilities having more than two patient support apparatuses 22. Indeed, location detection system 20 can be utilized with other devices besides patient support apparatuses 22, as mentioned previously.

Figure 6:
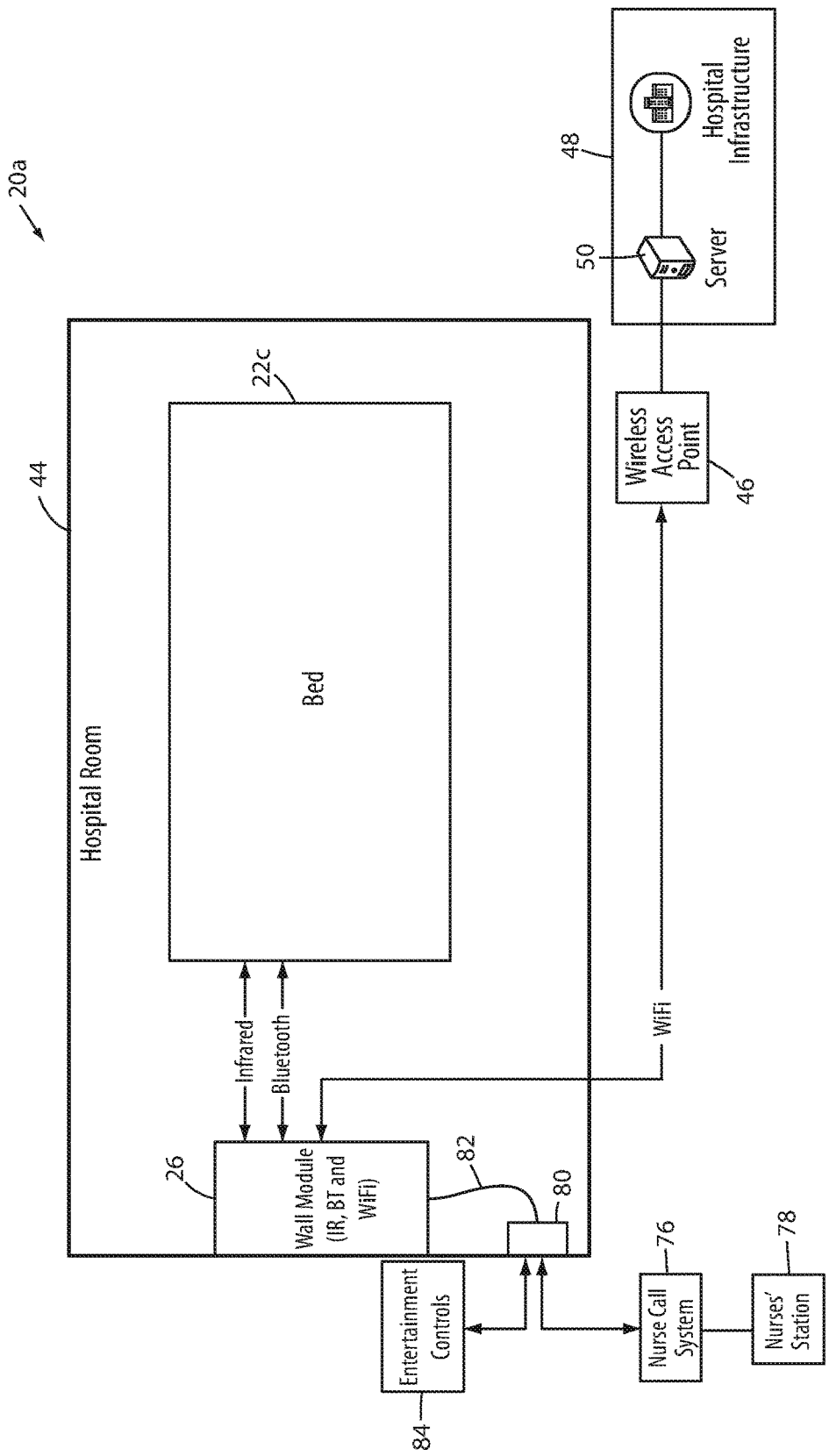
FIG. 6 is a block diagram of a modified location detection system shown with the patient support apparatus implemented as a bed and the system coupled to an illustrative example of a healthcare facility's IT infrastructure.
Figure 7:
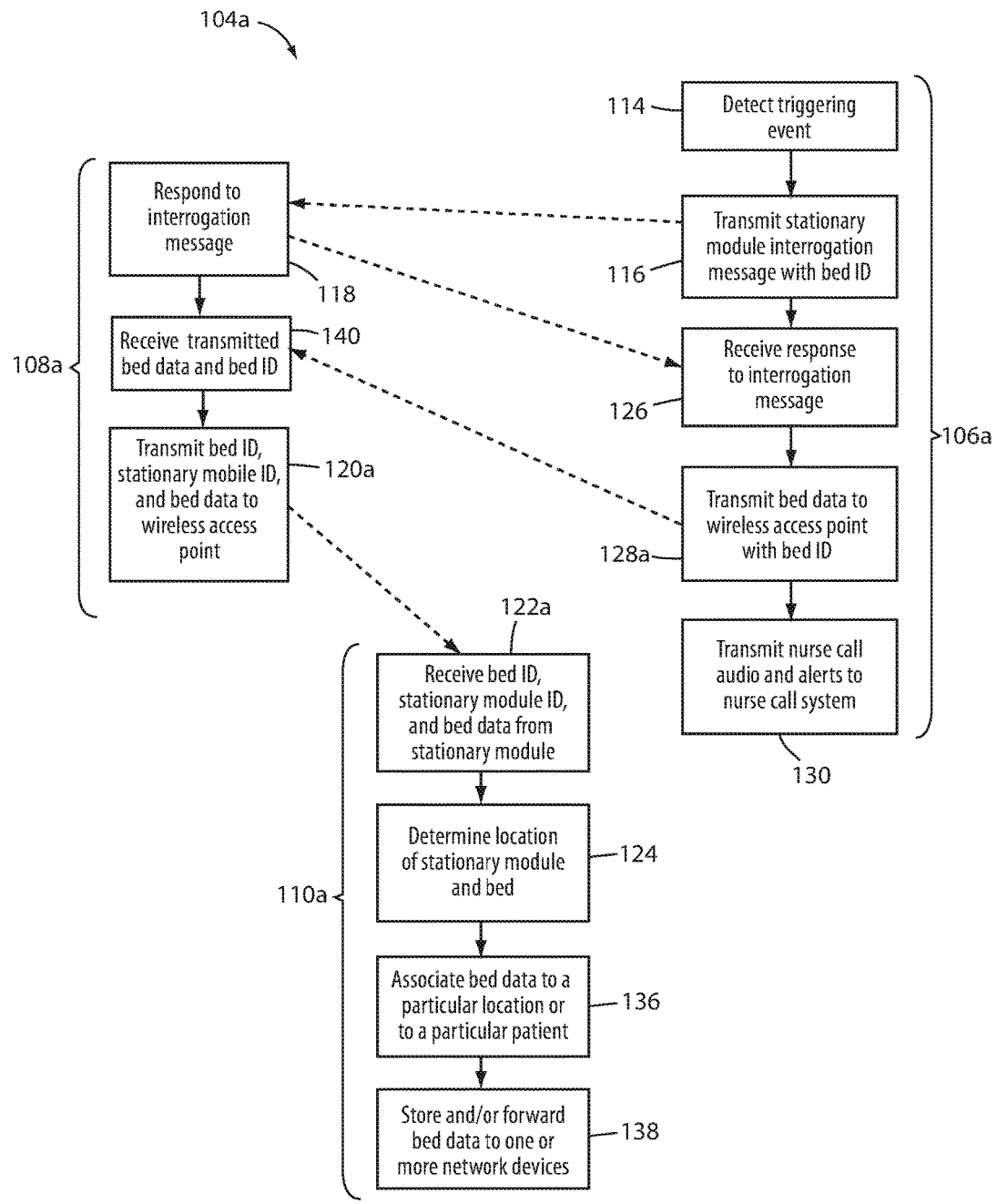
FIG. 7 is a flowchart of the location detection algorithm followed by the components of the modified location detection system of FIG. 6.

Another embodiment of a location detection system 20a is depicted in diagram form in FIG. 6. The location detection algorithm 104a followed by the components of location detection system 20a are shown in the flowchart of FIG. 7. Those components of location detection system 20a that are the same as the components of location detection system 20 are labeled herein with the same reference numbers as system 20. Similarly, those steps of algorithm 104a that are the same as the steps of algorithm 104 are labeled with the same reference numbers. Those components or steps of system 20a and algorithm 104a that have been modified in some fashion as compared to system 20 and/or algorithms 104 have been labeled with the same reference number followed by the letter "a." Finally, those components or steps of system 20a and algorithm 104a that are completely new have been provided a new reference number.

Location detection system 20a differs structurally from location detection system 20 in that patient support apparatus 22c does not include a WiFi transceiver 88a. Instead, patient support apparatus 22c communicates data to server 50 using stationary module 26 as an intermediary. This is described in greater detail below with respect to location detection algorithm 104a.

Location detection algorithm 104a differs from location detection algorithm 104 in that it includes modified steps 128a, 120a, and 122a, as well as new step 140. With reference to FIG. 7, algorithm 104a begins with a patient support apparatus algorithm 106a at step 114, which is the same as step 114 of algorithm 104, and need not be described further. Patient support apparatus algorithm 106a then proceeds to steps 116 and 126, which are the same as previously described. Patient support algorithm 106a differs from algorithm 106 when it reaches modified step 128a. At step 128a, patient support apparatus transmits the patient support apparatus data wirelessly to stationary module 26 using, in at least one embodiment, Bluetooth transceiver 86a. This differs from step 128 where patient support apparatus 22 transmits its patient support apparatus data to wireless access point 46 (and from there to server 50) using WiFi transceiver 88a. Thus, algorithm 106a differs from algorithm 106 in that patient support apparatus 22c transmits its data to stationary module 26 using a Bluetooth transceiver 86a, rather than to wireless access point 46 using a WiFi transceiver 88a (which patient support apparatus 22c does not have, as noted above).

Stationary module algorithm 108a differs from algorithm 108 in that it includes the new step 140 of receiving the transmitted patient support apparatus data from patient support apparatus 22c. This transmitted data includes the patient support apparatus identifier 96. Upon receiving this data at step 140, controller 112 of stationary module 26 proceeds to modified step 120a, where it transmits—in addition to patient support apparatus identifier 96 and stationary module identifier 98—the patient support apparatus data received at step 140. These items—identifiers 96, 98, and the patient support apparatus data—are transmitted at step 120 to wireless access point 46 via WiFi transceiver 88b on board stationary module 26. The patient support apparatus data includes any of the data previously mentioned and described above with respect to algorithm 104.

Server algorithm 110a includes the same steps as server algorithm 110 with the exception of a modified step 122a and the omission of step 134. Step 122a differs from step 122 in that server 50 also receives at step 122a the patient support apparatus data from stationary module 26. As shown in FIG. 4, this patient support apparatus data is received by server 50 at step 134 from patient support apparatus 22 itself in algorithm 104. The patient support apparatus data therefore follows a different path to server 50 in algorithm 104a than it follows in algorithm 104.

It will be understood that the transmission of patient support data at steps 128, 128a in both algorithms 104 and 104a may take place repetitively. That is, the transmitted data can occur repeatedly while the patient support apparatus 22, 22a-c is positioned at particular location. It is not necessary for another triggering event to occur at step 114 before such additional data is transmitted. Thus, for example, when any status data regarding patient support apparatus 22, 22a-c, or the patient associated therewith changes, additional data may be transmitted off of patient support apparatus 22, 22a-c.

It will further be understood that the transmission of nurse call audio and alerts to nurse call system 76 at step 130 of algorithm 104a can occur in either of two ways—as described previously with respect to algorithm 104—depending upon whether cable 82 is coupled between stationary module 26 and headwall connector 80 or between patient support apparatus 22, 22a-c and headwall connector 80.

Figure 8:
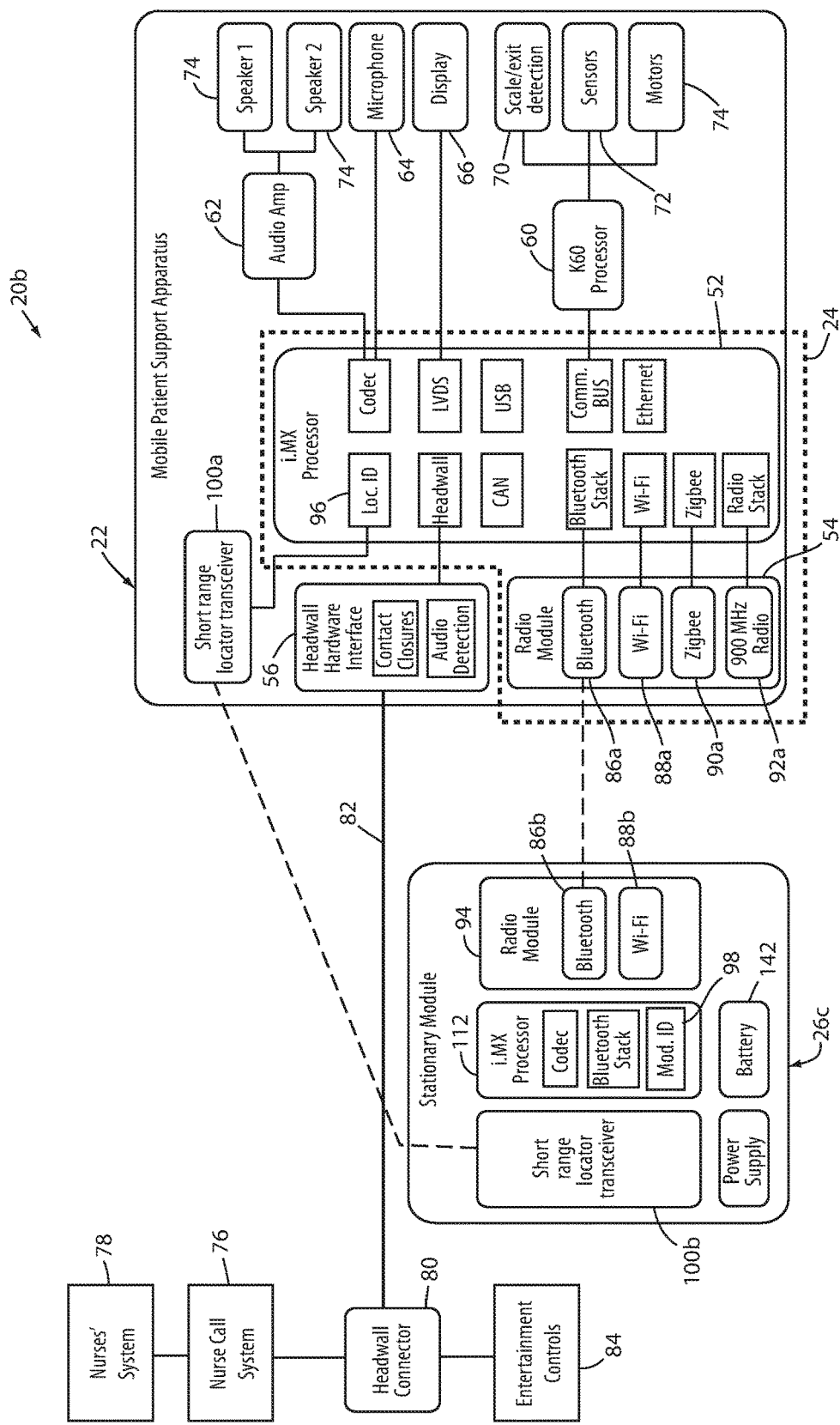
FIG. 8 is a block diagram of the internal components of the various structures of yet another modified location detection system.

FIG. 8 illustrates the internal details of another modified location detection system 20b. Those components of location detection system 20b that are the same as the components of location detection systems 20 and/or 20a are labeled herein with the same reference numbers as systems 20 and/or 20a. Those components of system 20b that have been modified in some fashion as compared to systems 20 and/or 20*a* have been labeled with the same reference number followed by the letter "a" or "b."

Location detection system 20*b* differs from location detection systems 20 and 20*a* in that it includes a modified stationary module 26*c*. Stationary module 26*c* differs from stationary module 26 in that it does not include a headwall hardware interface 132. Stationary module 26*c* therefore is not capable of receiving a nurse call cable 82. As a result, stationary module 26*c* does forward any data received from patient support apparatus 22 onto headwall connector 80. Any data or messages from patient support apparatus 22 that are destined to headwall connector 80 (and any of the downstream components, such as nurse call system 76, nurses' station 78, and/or the entertainment controls 84) are transmitted from patient support apparatus 22 via cable 82. All of the other components of stationary module 26*c* are the same as the components of stationary module 26.

Location detection system 20*b* may follow either location algorithm 104 or location algorithm 104*a*. The only modification to these algorithms is that step 130 is carried out via the cable 82 running from patient support apparatus 22 to connector 80, rather than wirelessly, as is an option for location detection systems 20 and 20*a*. This is because, as noted, stationary module 26*c* does not include structure for receiving a cable 82 and therefore all communication between patient support apparatus 22 and nurse call system 76 (or the entertainment controls 84) bypasses stationary module 26*c* via cable 82.

It will be understood by those skilled in the art that various other modifications may be made to location detection systems 20, 20*a*, and 20*b*. For example, in one such modification, the data table or map that correlates the identifiers of each stationary module 26 (or 26*c*) within the healthcare facility is stored onboard each patient support apparatus 22. In such modified embodiments, the step of associating a patient support apparatus 22 to a particular location—which is carried out in step 136 by server 50 in algorithms 104 and 104*a*—is carried out by patient support apparatus 22 (or 22*a-c*). With such a modification, it is not necessary for patient support apparatus 22, 22*a-c*- to transmit its identifier 96 to wireless access point 46 or to server 50. Instead, any data or messages that are to be communicated from patient support apparatus 22, 22*a-c* to wireless access point 46 and/or to server 50 are instead transmitted with the location of patient support apparatus 22, 22*a*. In other words, instead of transmitting its identifier with each message, patient support apparatus 22, 22*a-c* transmits its location with each message. The transmitted location may be a room number, or it may be the combination of a room and a bed bay identifier within the room. In still other situations, stationary modules 26, 26*c* may be positioned at locations other than in rooms, and the transmitted location may take on other forms, such as "hallway X," or "elevator Y," or still other forms.

When server 50 receives the messages and data from the patient support apparatus 22, 22*a-c*, it uses the location information transmitted therewith to correlate the transmitted messages and/or data with the correct patient. That is, as noted previously, server 50 either contains, or has access to, a database that identifies patients according to their room number and/or bed bay number. By determining the patient from the transmitted location, server 50 is able to determine, for example, what electronic medical record to file certain the receiving information with and/or what caregiver is assigned to that patient, and/or still other information.

In any of the various embodiments described herein, radio modules 54 and 94 include transceivers that are able to transmit binary data packets at a rate of at least 10 kilobits per second with a delay of less than 100 milliseconds. Further, the modules include transceivers that are used to communicate audio signals and that have a bandwidth of at least 8 kilohertz and transmits the audio signals with less than 400 milliseconds of delay. Other bandwidths and delay thresholds can, of course, be used for either or both sets of transceivers.

In still other embodiments, stationary module 26 may be modified so as to communicate wirelessly with headwall connector 80, instead of using cable 82. Such wireless communication between stationary module 26 and headwall connector 80 is described in more detail in commonly assigned U.S. patent application Ser. No. 62/035,656 filed Aug. 11, 2014 by inventors Krishna Bhimavarapu et al. and entitled PATIENT SUPPORT APPARATUSES WITH WIRELESS HEADWALL COMMUNICATION, the complete disclosure of which is hereby incorporated herein by reference.

In still other embodiments, mobile wireless unit 24 is a unit that is physically separate from patient support apparatus 22, 22*a-c* but is adapted to be selectively plugged into and unplugged from patient support apparatus 22, 22*a-c* (such as, but not limited to, a dongle). For example, in one embodiment, mobile wireless unit 24 is plugged into the connector in headwall hardware interface 56 that is otherwise used to couple cable 82 between patient support apparatus 22, 22*a-c* and connector 80. Thus, if a wireless connection to connector 80 is desired, mobile wireless unit 24 is plugged into headwall hardware interface 56 instead of a cable. This enables wireless communication between patient support apparatus 22, 22*a-c* and stationary module 26 without having to make any modifications to patient support apparatus. When so constructed, mobile wireless unit 24 can therefore be used to convert existing patient support apparatuses 22 that do not include wireless communication abilities into patient support apparatuses that are capable of wireless communication. Further, when so constructed, mobile wireless unit 24 communicates with main controller 60, audio amplifier 62, and mobile locator transceiver 58 via headwall hardware interface 56, rather than directly (as it does in the embodiment shown in FIG. 2).

It will be understood that radio modules 54 and 94 can be modified to include a different number of transceivers than what is shown in FIG. 2, as well as one or more transceivers that use different wireless communication protocols from those shown in FIG. 2. It will also be understood that the use of the term "transceiver" herein is intended to cover not only devices that include a transmitter and receiver contained within a single unit, but also devices having a transmitter separate from a receiver, and/or any other devices that are capable of both transmitted and receiving signals or messages.

In at least one embodiment, in addition to sending signals received from mobile wireless unit 24 of patient support apparatus 22 to headwall connector 80, stationary module 26 is also adapted to forward signals received from headwall connector 80 via cable 82 to mobile wireless unit 24 of patient support apparatus 22. Stationary module 26 is therefore adapted, in at least one embodiment, to provide bidirectional communication between patient support apparatus 22 and headwall connector 80. Such bidirectional communication includes, but is not limited to, communicating audio signals between a person supported on patient support apparatus 22 and a caregiver positioned remotely from patient support apparatus 22 (which is accomplished by stationary module 26 forwarding the audio signals of the person on patient support apparatus 22 to nurse call system 76, and vice versa).

As was noted above with respect to algorithms 104 and 104a, patient support apparatuses 22, 22a-c are adapted to transmit patient support apparatus data in steps 128 and 128a, respectively. In algorithm 104, this status data is transmitted to server 50 via WiFi transceiver 88a on-board the patient support apparatus, which forwards the data to a wireless access point 46, which in turn forwards it to 50. In algorithm 104a, this status data is first transmitted to stationary module 26 via Bluetooth transceiver 86a, and stationary module 26 then transmits this data to server 50 via its own WiFi transceiver 88b. In at least some embodiments, patient support apparatuses 22, 22a-c are adapted to also transmit some or all of this status data to nurse call system 76. In such embodiments, this data is transmitted to nurse call system 76 in one of two ways, depending upon whether cable 82 is coupled to patient support apparatus 22, 22a-c or to stationary module 26. When cable 82 is coupled to the patient support apparatus, controller 52 sends this data, or a portion of it, to headwall hardware interface 56, which then forwards the data via cable 82 to connector 80, from which it then travels to nurse call system 76. When cable 82 is coupled to stationary module 26, controller 52 sends this data, or a portion of it, to radio module 54, which then forwards it via Bluetooth transceiver 86a to stationary module 26. Stationary module 26 then forwards it to its own headwall hardware interface 132 (FIG. 2), which passes the data via cable 82 to connector 80 and nurse call system 76.

In such embodiments, it can therefore be seen that at least some of the data transmitted at step 128 of algorithm 104 is sent off of the patient support apparatus 22, 22a-b via two different methods. One such method is the transmission of the data by way of headwall hardware interface 56, cable 82, and connector 80 to nurse call system 76 (or alternatively by way of Bluetooth transceiver 86a, stationary module 26, headwall hardware interface 132, and connector 80 to nurse call system 76). Another such method is the transmission of the data by way of WiFi transceiver 88a and wireless access point 46 to server 50.

It can also be seen that at least some data transmitted at step 128a of algorithm 104a is sent off of the patient support apparatus 22c via two different methods, in at least some embodiments. One such method is the transmission of the data by way of headwall hardware interface 56, cable 82, and connector 80 to nurse call system 76. Another such method is the transmission of the data by way of Bluetooth transceiver 86a, stationary module 26, WiFi transceiver 88b, and wireless access point 46 to server 50.

Still further, it can also be seen that, at least in some embodiments, patient support apparatuses 22, 22a-c are adapted to transmit the same data to two different locations. In such embodiments, some of the data is transmitted to nurse call system 76 and some of the same data is transmitted to server 50. Still further, in some embodiments, the transmission of the data to these two different locations is accomplished via the patient support apparatus transmitting the data via different on board transceivers (e.g. Bluetooth transceiver 86a, WiFi transceiver 88a, and/or headwall hardware interface 56), while in other embodiments, the patient support apparatus 22 transmits the data only once to stationary module 26 and stationary module 26 splits the data for forwarding to both nurse call system 76 and to server 50.

In the embodiment of location detection system 20 shown in FIGS. 2-5, stationary module 26 communicates the data and signals it receives from mobile wireless unit 24 to connector 80 by directing the incoming data and signals it receives to the appropriate pin or pins of headwall connector 80. For example, when headwall connector 80 includes 37 sockets for coupling to a 37 pin plug, or vice versa, it is common for pin numbers 30 and 31 of connector 80 to be used for indicating a "priority alert," which is often synonymous with an alert that is issued when a patient exits from patient support apparatus 22. Further, depending upon the particular configuration that has been implemented at a particular healthcare facility, the connection between pin numbers 30 and 31 may be normally open or it may be normally closed. Regardless of whether it is normally open or normally closed, whenever stationary module 26 receives a message from mobile wireless unit 24 that a person has exited from patient support apparatus 22, stationary module 26 changes the status of pins 30 and 31 such that they switch from whatever state they are normally in to their opposite state. Stationary module 26 therefore reacts to the exit message it receives from mobile wireless unit 24 by either opening or closing pins 30 and 31. The nurse call system 76 that is communicatively coupled to headwall connector 80 interprets this opening or closing of pins 30 and 31 in the same manner as if a cable were coupled between patient support apparatus 22 and headwall connector 80, such as by sending the appropriate signals to one or more nurse's stations, flashing a light outside the room of patient support apparatus 22, forwarding a call to a mobile communication device carried by the caregiver assigned to the occupant of patient support apparatus 22, and/or taking other steps, depending upon the specific configuration of the nurse call system.

In addition to sending data indicating that an occupant of patient support apparatus 22 has exited, or is about to exit, from support surface 28, mobile wireless unit 24 is configured, in at least one embodiment, to wirelessly send to stationary module 26 at least the following additional messages: messages to turn on or off one or more room lights; messages to turn on or off one or more reading lights; messages to increase or decrease the volume of a nearby television set; messages to change a channel of the nearby television set; and messages containing audio packets generated from one or more microphones on the patient support apparatus 22 into which an occupant of patient support apparatus 22 speaks when desiring to communicate with a remote caregiver.

In other embodiments, mobile wireless unit 24 is configured to wirelessly send to stationary module 26 any one or more of the following messages, either in addition to or in lieu of any one or more of the messages previously mentioned: messages indicating the current status of one or more siderails 40 of patient support apparatus 22 (e.g. whether the side rails are up or down, or have changed position); messages indicating the current status of a brake on patient support apparatus 22; messages indicating the current status of the height of support surface 28 relative to base 32 (e.g. such as whether support surface 28 is at its lowest height or not); messages indicating the current angle of a head section of support surface 28 that is adapted to support a patient's torso and head; messages indicating the current status of exit detection system 70 (e.g. whether the exit detection system is armed or not); messages indicating the current charging status of one or more batteries on patient support apparatus 22; messages indicating the current status of an alternating current (A/C) power cable on patient support apparatus 22

(e.g. whether it is plugged in or not); diagnostic information about patient support apparatus 22; and/or any other messages containing information about patient support apparatus 22 which may be useful to communicate to a remote location.

In at least one embodiment, stationary module 26 is further configured to transmit information to headwall connector that does not originate from patient support apparatus 22, but instead is generated internally within stationary module 26. For example, in one embodiment, stationary module 26 is adapted to forward to headwall connector 80 an alert whenever the communication link between stationary module 26 and mobile wireless unit 24 is unintentionally lost. In other embodiments, stationary module generates any one or more of the following messages to be sent to mobile wireless unit 24: the charge status of a battery 142 (FIGS. 2, 8) contained within stationary module 26; acknowledgements of messages transmitted from mobile wireless unit 24 to stationary module 26; and messages used to establish, maintain, and disestablish the communication link between mobile wireless unit 24 and stationary module 26. Still other types of signals that originate from within stationary module 26 may also be sent to headwall connector 80.

When stationary module 26 is coupled via cable 82 to connector 80, it is also adapted, in at least some embodiments, to forward the following messages to wireless unit 24 based on information it receives from headwall connector 80: messages indicating the establishment and disestablishment of a nurse-call communication link (e.g. messages used for turning on and off a "nurse answer" light on patient support apparatus 22); and messages containing audio packets of a caregiver's voice (generated from a microphone into which the caregiver speaks and forwarded to the appropriate pins of connector 80).

It will be understood that, in those embodiments of location detection system 20 where patient support apparatus 22 communicates status data to stationary module 26, such as during step 128a of algorithm 106a (FIG. 7), patient support apparatus 22 can be configured to utilize the stationary module unique identifier 98 to ensure that patient support apparatus 22 does not communicate with an incorrect stationary module 26. For example, with specific reference to FIG. 5 where two stationary modules 26a and 26b are present in a single room 44, the acknowledgement from stationary module 26a that first patient support apparatus 22a receives at step 126 will include the unique identifier 98 of stationary module 26a. Patient support apparatus 22a uses this unique identifier 98 as an address in subsequent communications with stationary module 26a, such as during step 128a. The use of this unique identifier 98 ensures that, for example, if stationary module 26b inadvertently detects the transmission from patient support apparatus 22a to stationary module 26a, stationary module 26b will know that this message is not intended for it because it is addressed to stationary module 26a. The unique stationary identifiers can therefore be used to ensure that wireless messages between patient support apparatuses 22 and stationary modules 26 that use any of the longer range transceivers (e.g. not transceiver 100) are only acted upon by their intended recipients.

In some embodiments, when stationary module 26 are initially installed within a room of a healthcare facility, the unique identifiers 98 of the modules 26 are input into these modules 26. The inputting of this data into each of modules 26 may take on a variety of different forms, such as by setting appropriate dip switches on each of module 26 that corresponds to their unique identifier 98; uploading the unique identifiers 98 via a USB port, or other type of electronic port, integrated into each stationary module 26; having each stationary module 26 connect to a server on a local area network using, for example, WiFi transceiver 88b, and downloading from the server the corresponding unique identifiers 98; or by other means. Regardless of the manner of inputting this information, each stationary module 26 is configured during set-up to have stored in its memory a unique identifier 98 that distinguishes itself from the unique identifiers 98 of the other stationary modules 26.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A location detection system comprising:
   stationary module positioned at a known location within a facility, the stationary module including a first unique identifier and a first wireless transceiver adapted to transmit the first unique identifier; and
   a mobile patient support apparatus having a second unique identifier and a second wireless transceiver, the mobile patient support apparatus adapted to receive the first unique identifier from the stationary module, the mobile patient support apparatus further including a data table that correlates the first unique identifier to the known location within a healthcare facility, the mobile patient support apparatus adapted to transmit the known location to a wireless access point of a computer network using a third wireless transceiver, and the mobile patient support apparatus adapted to only transmit the known location to the wireless access point of the computer network if the mobile patient support apparatus and the stationary module successfully link to each other utilizing fourth and fifth wireless transceivers, the fourth and fifth wireless transceivers having a shorter communication range than the first and second wireless transceivers.

2. The location detection system of claim 1 wherein the first and second wireless transceivers operate in accordance with Institute of Electrical and Electronics Engineers (IEEE) standard 802.15.1, and the third wireless transceiver operates in accordance with IEEE standard 802.11.

3. The location detection system of claim 1 wherein the mobile patient support apparatus is adapted to receive the data table from a server coupled to the computer network, the mobile patient support apparatus receiving the data table via the third wireless transceiver.

4. The location detection system of claim 3 wherein the mobile patient support apparatus requests the data table from the server in response to a triggering event.

5. The location detection system of claim 1 wherein the data table correlates the first unique identifier to a room number of the healthcare facility.

6. A location detection system comprising:
a mobile patient support apparatus having a first unique identifier and a first wireless transceiver, the mobile patient support apparatus adapted to transmit the first unique identifier via the first wireless transceiver; and
a stationary module positioned at a fixed location within a healthcare facility, the stationary module including a second unique identifier and a second wireless transceiver adapted to receive the first unique identifier from the mobile patient support apparatus, the stationary module also including a data table that correlates the first unique identifier to the fixed location within the healthcare facility, and the stationary module being adapted to transmit the fixed location and the first unique identifier to a wireless access point of a computer network using a third wireless transceiver, wherein the stationary module is adapted to only transmit the fixed location and the first unique identifier to the wireless access point of the computer network if the mobile patient support apparatus and the stationary module successfully link to each other utilizing fourth and fifth wireless transceivers, the fourth and fifth wireless transceivers having a shorter communication range than the first and second wireless transceivers.

7. The location detection system of claim 6 wherein the stationary module is adapted to transmit the fixed location to the mobile patient support apparatus via the second wireless transceiver.

8. The location detection system of claim 6 wherein the first and second wireless transceivers operate in accordance with Institute of Electrical and Electronics Engineers (IEEE) standard 802.15.1, and the third wireless transceiver operates in accordance with IEEE standard 802.11.

9. The location detection system of claim 6 wherein the stationary module is adapted to receive the data table from a server coupled to the computer network, the stationary module receiving the data table via the third wireless transceiver.

10. The location detection system of claim 6 wherein transmitting the fixed location to the wireless access point includes transmitting a room number of a room that includes the fixed location.

* * * * *